US006617356B2

(12) United States Patent
Goodman et al.

(10) Patent No.: US 6,617,356 B2
(45) Date of Patent: *Sep. 9, 2003

(54) GEL SYSTEM FOR ORAL AND TOPICAL ADMINISTRATION OF WATER INSOLUBLE AND/OR WATER INTOLERANT DRUGS AND SUPPLEMENTS

(76) Inventors: Louis P. Goodman, 25 Sandalwood Dr., Parsippany, NJ (US) 07054; Dennis Bizub, 126 Ridge Ave., Bloomfield, NJ (US) 07003

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/476,352

(22) Filed: Jan. 3, 2000

(65) Prior Publication Data

US 2001/0006671 A1 Jul. 5, 2001

(51) Int. Cl.⁷ ............... A61K 31/195; A61K 31/00; A61K 35/78; A61K 47/00
(52) U.S. Cl. ............... 514/565; 424/752; 424/755; 424/757; 424/764; 514/23; 514/60; 514/561; 514/563; 514/613; 514/634; 514/665; 514/709; 514/711; 514/770; 514/777; 514/778; 514/783; 514/944; 514/969
(58) Field of Search ............... 424/439, 93.4, 424/93.45, 93.44, 93.51, 600, 617, 195.1, 724, 731, 752, 757, 764, 755; 426/72, 74, 519, 573; 514/25, 53, 60, 61, 63, 458, 492, 561, 562, 579, 613, 706, 770, 783, 944, 565, 563, 634, 665, 709, 711, 777, 778, 969, 23

(56) References Cited

U.S. PATENT DOCUMENTS

| 4,518,696 A | * | 5/1985 | Gehrman et al. ......... 435/252.9 |
| 5,122,377 A | * | 6/1992 | Miller et al. ................ 424/439 |
| 5,976,560 A | * | 11/1999 | Han et al. ................... 424/401 |

* cited by examiner

Primary Examiner—Michael G. Hartley
Assistant Examiner—Frank Choi
(74) Attorney, Agent, or Firm—Evelyn M. Sommer

(57) ABSTRACT

Suspensions, emulsions or dispersions of therapeutically active agents which are water insoluble or water intolerant such as nutritional supplements, herbal products, drugs, bacteria, yeast, vitamins and minerals are prepared as suspensions in edible vegetable oils such as orange, lemon, soybean, cotton seed, peanut, canola corn oil, sunflower, safflower, palm kernel, palm and coconut. The active therapeutic agent may be in crystalline or amorphous form, it may be a liquid as for example an oil such as vitamin B or beta carotene, or a preparation of a comminuted plant structure such as flower, parts, leaf; stern, root or tree bark, or an extract of a dried plant structure or a freeze dried preparation of a vital bacteria or yeast. The suspension is formed by active mixing of the active agent and oil. To the suspension of the active agent in vegetable oil is added tile silicon dioxide while actively mixing at 2000–4000 rpm to provide a stable gel, the active agent being uniformly distributed throughout the gel. Two to 60 minutes of stirring is more than adequate for all systems. The compositions can be administered orally, sublingually, buccally and topically. For topical administration the preparation of the invention may be formulated as a cream or ointment.

9 Claims, No Drawings

GEL SYSTEM FOR ORAL AND TOPICAL ADMINISTRATION OF WATER INSOLUBLE AND/OR WATER INTOLERANT DRUGS AND SUPPLEMENTS

The present invention relates to a new drug delivery system, a method for suspending both water insoluble and water intolerant materials in edible oils and products based thereon which are stable over prolonged periods of time and are well suited as for oral and topical administration. The method of the invention has particular advantage when the material involved undergoes changes disadvantageous to its intended application on direct exposure to water. Such materials include creatine, various Lactobacillus species, herbal products, vitamins, etc. It is therefore desirable to have a product which can be delivered in its active state without the use of water in its preparation, which is stable, readily taken up by the body and provided in practical concentrations.

The drug delivery system of the invention comprises an edible oil to which a gelling agent, such as silicon dioxide is added. This system allows for uniform suspensions of the active agent, facilitating drug delivery as well as in some instances regulating the rate of drug delivery. The active agent is incorporated into the oil-gelling agent preparation providing formulations for therapeutic use.

The method of the invention comprises a series of steps whose sequence can be varied. In accordance with one embodiment of the invention, the active material is introduced into the vegetable oil under conditions for forming a uniform dispersion, emulsion or suspension and then a silica product, namely silicon dioxide is introduced to form a pourable gel again under conditions whereby a stable uniform thickened suspension of the active material in the gel will result. Alternatively the silica dioxide can be added to the oil, and the active material then introduced into the thickened mixture to form the suspension of the active material in the carrier gel.

The edible vegetable oils suitable for use herein include soybean, corn, orange and citrus oils, cottonseed, olive oil, peanut oil, sunflower oil, safflower oil, coconut oil, canola oil, palm kernel oil, palm oil. Mineral oils of varied molecular weights can also be used for some preparations. Mineral oil is a standard ingredient in commercially available creams, ointment-type bases, as for example available from Schering and is frequently used in topical drug delivery systems. Mineral oil can also be used for oral ingestion. It has the advantage of being non-caloric and is without toxicity unless taken in large doses. The vegetable oils mentioned are known food, nutritional supplement and drug components and are especially suitable for use in the invention. Natural gums such as acacia or tragacanth can be added to the combination of oil, active ingredient and silica product primarily to aid in suspension of the insoluble pharmacologically active or nutritional supplement substance in the oil. Substances such as synthetic mucilagenous materials including polyvinyl alcohol, methyl cellulose and carboxymethyl-cellulose can be used in a similar manner to the natural gums. The synthetic gums have the advantage of not being glycogenetic. The colloidal character and viscosity of the gums contribute further towards preventing sedimentation of the suspended agents.

The dispersions or suspensions of the invention can be prepared by dispersing the silicon dioxide product in the oil. As a rule, the dispersal step, e.g., treatment with a high angular speed agitator, and the active ingredient then dissolved or dispersed in the gel formed after the initial dispersal step. The second dispersal step can be carried out using the same stirrer, or other conventional type homogenizing or emulsifying equipment. A suspension of the active agent in the pourable gelled oil is thus formed. This suspension has a suitably long shelf life and can be used directly for its application. When administered perorally, this suspension is used in a manner consistent with the type of effective substance present, the amount of effective substance present and the therapeutic dose which is commonplace for such administration. It is also possible to reverse the sequence by forming first the dispersion of active ingredient in the oil, followed by a second dispersal step in which the silicon dioxide is introduced and distributed forming the gelled product.

In accordance with one embodiment of the invention the silica product can be added in increments so that a first amount is added to the oil suspension and then a second amount of silica product, preferably silicon dioxide, introduced again under conditions for ensuring the formation of a stable thickened suspension of the active material in the gel.

A thixotropic gel is formed through the mechanism of hydrogen bonding between the silica and active materials added. The gel suspends the ingredients that would normally precipitate or settle out. The resultant stable suspensions contain the active material in discrete amounts in unaltered form. The gel suspensions are suitable for oral and topical administration and can be use per se or with the addition of the conventional adjuvants, colorants, flavorants etc.

Silicon dioxide or fumed silica the preferred gelling agent is characterized by extremely small particle size, its enormous surface, high purity and its chain forming tendencies. Silicon dioxide is produced by the vapor phase hydrolysis of silicon tetrachloride in a hydrogen-oxygen flame. The combustion process creates silicon dioxide molecules which condense to form particles. The particles collide, attach and sinter together resulting in a three-dimensional branched chain aggregate. Once the aggregates cool further collisions result in mechanical entanglement of the chains, termed agglomeration. The resulting white powder is of agglomerate size of less than 325 US mesh (44 microns).

The surface chemistry of silicon dioxide is extremely important especially in relation to its ability to thicken non-polar and semi-polar liquid systems. During the preparation of silicon dioxide, hydroxyl groups become attached to some of the silicon atoms of the particle surface making it hydrophilic and capable of bonding with suitable molecules of material in vapor, liquid or solid form. The surface OH groups are capable of forming H bonds between silicon dioxide aggregates. This network increases the viscosity of the system and produces thixotropic behavior. Thixotropic behavior is the time dependent recovery of viscosity after shearing (shearing forces due to mixing). The viscosity decreases in proportion to the length of time of mixing or the intensity of the mixing. Once the shearing force has been removed, the bonds rebuild over time and the viscosity approaches its original value. The presence of these OH groups is the key to the mechanism through which silicon dioxide is able to perform many of its functions. The most important and widespread use of silicon dioxide in liquid systems is for the control and increase of viscosity and thixotropy. A major determinant of the effect of silicon dioxide will produce in any system is the nature of the solvent or suspending material used. Network formation is determined to a large degree by the capability of the solvent or suspending agent to participate in the formation of hydrogen bonds. Heretofore this capacity of silicon dioxide has not been applied to the thickening of oils or for the purpose of producing stable suspensions of water-soluble, water insoluble and water intolerant drugs and supplements suitable for oral and topical administration.

In accordance with the invention, the suspending medium can be grouped into three classifications. It is in the non-hydrogen-bonding systems (class 111) that silicon dioxide displays its greatest efficiency, the silica particle has no choice but to hydrogen bond with other silica particles and the greatest degree of network formation is achieved at the lowest concentration of silicon. Concentrations of 3% to 6% silicon dioxide by weight are usually sufficient to provide fairly thick gel formations, smaller concentrations will provide any viscosity required up to the stage of gelation. Examples of suspending agents suitable for use therein are the mineral oils, vegetable oils, etc.

In medium hydrogen bonding systems (class 11) silicon dioxide is slightly less efficient than the non-hydrogen-bonding systems. Usually the level of silicon needed for gel formation is 5 to 10 weight percent. Examples of solvents and suspending media in this class also include vegetable oils, including peanut, corn, canola, olive, soy, orange and lemon oils, sunflower, safflower, coconut, palm and palm kernel.

In highly hydrogen-bonding systems (class 1) a much higher concentration of silicon dioxide will be required to produce a given increase in viscosity and thixotropy. A silicon load as much as 10 to 15 weight % may be required.

Maximum viscosity of silicon dioxide, 2% by weight is obtained quickly after vigorous mixing for example using a rotor stator high speed stirring apparatus, high angular speed agitator or blender.

The following is a comparison of viscosities characteristically obtained with the different classes of suspending media:

Mineral Oil class 111–1–4% by weight of silicon dioxide produced a Brookfield viscosity of 1,000 to 70,000 cps.

Vegetable Oil class 11–1–4% by weight of silicon dioxide produced a Brookfield viscosity of about 1000 cps, 6–8% about 10,000 cps.

Viscosity values are in centipoises (cps) as measured using a Brookfield viscometer at 6 rpm at room temperature and in one minute. Viscosities then level off for group 11 and 111 agents and do not change substantially with time. The viscosity is unchanged through pH 1 to 9 but will fall off with higher pH values.

Silicon dioxide has been widely used in foods, pharmaceuticals, animal feeds, cosmetics, etc.

Extensive toxicological studies indicate that silicon dioxide does not possess the fibrogenic potential of crystalline silicas. Tests for acute oral toxicity, primary dermal irritation, primary eye irritation, and mutagenic tests indicate that silicon dioxide is inert.

Silicon dioxide meets the USP National Formulary requirements for purity. It has been authorized by the FDA for cosmetic applications. It has been approved by the FDA for food use up to 2 weight percent, for pharmaceutical use up to 3 weight per cent in internal applications and up to 8 weight percent in pharmaceutical products for use in topical applications. It is classified as a non-hazardous, non-restrictive substance under the provisions of the Hazardous Materials Act (P.L. 93-633).

Silicon dioxide is a unique, amorphous, of extremely high purity, sub-micron size material and has been approved by the FDA. Some of its particularly important properties for use in medicinal preparations intended for topical and oral use include silicon dioxide's fine particle size, high purity, amorphous structure, chemically inertness, non-toxicity, that it is easily handled and dispersed, and is colorless, odorless and tasteless.

In accordance with the invention silicon dioxide is used as a suspending or anti-settling agent for many different types of applications including suspension of solids in liquids or for the suspension of liquids in liquids (emulsions). The suspending ability of silicon dioxide is a result of the formation of a network when it is dispersed in a liquid. The network serves to keep droplets of particles separated from each other so that they cannot readily coalesce and undergo phase separation or settle out. The increased viscosity of the system helps to impede the rate of movement of all the ingredients in the mixture. Silicon dioxide is available in a number of grades which are suitable for use in the invention. These grades vary with the surface area of the aggregates and the degree of compression of the final product. The grade preferably used in the invention has a surface area (m 2/g) of 200±25. Chemical and physical analysis indicates that the percent silicon dioxide present in the product is greater than 99.8% and that the average particle size (aggregate) is ±0.2 to 0.3 microns.

A large number of pharmacologically active preparations can be prepared by the method of this invention; of particular interest are the following:

Creatine ($C_4H_9N_3O_2$) which is a normal constituent of muscle, brain and blood, is involved in energy storage in skeletal muscle and other tissues. Creatine is synthesized in the liver from amino acids and then transported by the blood to the muscle. There the enzyme creatine phosphokinase catalyzes the reaction of creatine with ATP to form phosphocreatine. Phosphocreatine contains a high energy $PO_4$ bond and serves as an energy storage mechanism. Creatinine is a catabolic end product, an anhydride of creatine (or phosphocreatine) produced by the loss of water (or phosphoric acid) from the molecule in an irreversible reaction. Creatinine is not reutilized, but is excreted via the urine. It is formed at a nearly constant rate which is proportional to the body muscle mass. Numerous studies have shown that the use of oral creatine supplementation in doses of 20 grams creatine monohydrate per day for five days produces an increase in muscle total creatine concentration as well as a cumulative increase in both peak and total work production.

The propensity for creatine to convert to creatinine in a water based solution can be avoided by the method of this invention, i.e., by forming in accordance with one embodiment of the invention a suspension of silicon dioxide in vegetable oil followed by addition of creatine monohydrate. The user can use the liquid gelled suspension directly and does not have to suspend a powder in a liquid such as water, juice or the like before utilization.

In accordance with another embodiment of the invention, creatine monohydrate is combined with one of the 20 amino acids and/or sugars which can be a monosaccharide, disaccharide, trisaccharide or polysaccharide.

Examples of the monosaccharides which are suitable are the pentoses including D-arabinose, L-arabinose, D-ribose, 2 deoxyribose, D-xylose and D-erythropentulose.

Examples of monosaccharide hexoses which can be used in the invention are D-galactose, L-galactose, D-glucose, D-mannose and D-fructose.

Examples of disaccharides include maltose, α,α trehalose and sucrose.

An example of trisaccharide is raffinose which is found in sugar beets.

Polysaccharides which can be advantageously used are starch and glycogen.

Any of the amino acids which are conventionally used in food and nutritional supplements can be used for combination with the creatine monohydrate. Combinations of creatine monohydrate with a saccharide as above exemplified may be used in sports nutrition for achieving optimal performance.

It is well recognized by those versed in the art that the amino acids can be replaced by full proteins or partially digested proteins such as peptides.

Lactobacillus This term generally designates catalase negative, gram positive, non-motile rods that grow aerobically and ferment carbohydrates, either homofermentatively to lactic acid or heterofermentatively into lactic acid and other products including carbon dioxide.

Four species of lactobacillus are preferred for use in the invention, namely *Lactobacillus acidophilus, Lactobacillus rhamnosus, Lactobacillus casei,* SPP *Para casei* and *Lactobacillus bulgarious.*

*Lactobacillus acidophilus* is an inhabitant of the small intestine in humans. Acidophilus manufacture lactase to digest milk sugar and produces lactic acid, which serves to suppress undesirable bacteria and yeasts. Some strains are reported to produce natural antibiotics, to lower cholesterol levels and to kill yeasts such as Candida. *Lactobacillus bulgaricus* is a transient but very important bacterium which by manufacturing lactic acid, in the gastrointestinal tract encourage a good environment for the resident bacteria such as acidophilus.

Bifidobacterium bifidum and Bifidobacterium longum.These bacteria are the main inhabitants of the large intestine and are also found in the lower part of the small intestine and vagina. They produce a number of specialized acids, which act to prevent colonization of the large intestine by invading bacteria, yeasts and viruses. They also prevent toxicity from nitrates in food and assist in the manufacture of B vitamins.

Enterococcus. A genus of gram-positive bacteria which belong to the family Streptococcaceae. Of the 12 species two are found in the human gastrointestinal tract. They are amphiobiotic without clearly defined primary pathogenicity.

Yeasts. The yeast's are an effective food supplement. They produce B 1 and B 2 vitamins and niacin and other B complex vitamins.

It is well recognized that it is advantageous to have these microflora in the intestine. These microorganisms are available as freeze-dried powders that are generally and heretofore have been ingested after first mixing with milk or juice at the time they are to be consumed. In some preparations the organisms are dispensed in capsule form. They cannot be dispensed suspended in water and kept for any length of time, as they will continue to divide and eventually die in their own waste products as they become too numerous for the solution they are suspended in. The method of this invention, suspension in oil of the silicon dioxide gelling agent and then the addition of the lyophilized bacteria avoids the death of the organism and doesn't allow the organism to grow until it reaches the intestine.

The usual dose of organisms is about 20 million to 400 million organisms (CFU).

Any number of medicinal herb products can also be prepared by the method of the invention. Among the preferred are:

Hypericum Perforatum (St.John's Wort). St.John's Wort consists of the dried above ground parts of Hypericum perforatum gathered during flowering season. The active ingredients are anthracene derivatives (0.1–0.15%), in particular hypericin flavonoids (2–4%), xanthenes, acylchloroglucinols, volatile oils, oligomeric procyanidines, catechin tannins and caffein acid derivatives. It acts as a mild antidepressant, sedative, and anxiolytic. It is also used for treatment of inflammation of the skin, and for treatment of wound injuries and burns. Studies have demonstrated that the antidepressant effect may be due to the presence of a monoamine oxidase inhibiting function in the active agents as well as the ability of the herb to inhibit the re-uptake of serotonin. Oily Hypericum preparations demonstrate an anti-inflammatory action due to their high flavonoid content.

The average daily dose of drug is 0.2 to 1.0 mg of total hypericin. This corresponds to 2 to 4 grams of herb powder. Standardized preparations of the dried herb product are calibrated to contain 0.15–0.3% hypericin; this would correspond to 1.5 to 3 grams of herb powder.

Ginkgo Biloba (Ginkgo). The medicinal parts are the leaves and the seeds separated from their fleshy outer layer. The active compounds are flavonoids, biflavonoids, proanthocyanidins, trilactonic diterpenes, and trilactonic sesquiterpene.

Ginkgo acts by inhibition of the development of traumatically or toxically induced cerebral edema and inhibition of cellular lesions in the retina by inhibition of age related reduction of muscarinergic cholinoceptors as well as stimulation of choline uptake in the hypo campus. Indications and usage are for brain dysfunction, including memory loss, symptomatic relief of intermittent claudication, vertigo of vascular origin, and tinnitus of vascular origin.

The average daily dose is 240–360 mg of dried extract. The dried extract is prepared from the dried Ginkgo biloba leaf and is manufactured using acetone/water extraction and subsequent purification steps. Generally ginkgo is taken in 2 or 3 doses, orally. Ginkgo preparations are available standardized to contain 24% ginkgo flavones glycosides; and the recommended dose of this preparation is 30–100 mg per dose.

Piper Methysticum (Kava-Kava). The medicinal parts are the peeled, dried cut rhizome with or without roots. The active ingredient is Kava lactone (Kava pyrones 5–12%). Comminuted rhizome and other galinic preparations are used in preparing pharmaceutical preparations.

The drug has anti-anxiety effects. It is indicated and used for nervousness and insomnia. The daily dose for herbs and extracts is the equivalent of 60 to 120 mg kava pyrones.

The method of this invention allows for combination of herbal products e.g., St.John's Wort and Ginkgo. A daily dose would be 300 mg of St. John's Wort (0.3% hypericin) and 60 mg Ginkgo Biloba. Another combination could be St. John's Wort and Kava Kava. A daily dose would be 300 mg St. John's Wort (standardized to 0.3% hypericin) and 250 mg Kava Kava (root powder).

Vitamins and Minerals. Vitamins and minerals could readily be dispensed by the method of the invention, either as a single vitamin or in combination with other vitamins and/or minerals. Listings of such vitamins and minerals and the percent Daily Values which have been determined by the National Research Council of the National Academy of Sciences are readily available in the literature along with their pharmacological action.

In accordance with yet another embodiment of the invention water-soluble materials such as creatine monohydrate, sugars, amino acids, water-soluble vitamins, etc., are combined with fat-soluble materials such as Vitamins A, D, E and K, Co-Enzyme Q-10, etc., into a matrix containing soybean oil and silicon dioxide.

A host of other biological active substances such as amino acids, melatonin, chitosan, other herbal products, etc., could be prepared in combination or as a single entity.

Drug absorption is determined by physicochemical properties of drugs, their formulations and method of administration. The actual dosage forms include liquid-liquid suspensions, liquid-solid dispersions liquid-liquid emulsions and semi-solids (creams, ointments), in a gel form. These dosage forms are formulated to be administered by various routes, including oral, buccal, sublingual, and, topical.

For oral administration, the most common route, absorption refers to the transport of drugs across the membranes of the epithelial cells in the gastrointestinal tract. The oral mucosa has a thin epithelium and a rich vascularity that favors absorption, but contact is usually too brief, even for drugs in solution, for appreciable absorption to occur. A drug administered by introduction between the gums and cheek (buccal administration) or under the tongue (sublingual administration) is retained longer so that absorption is more complete. Drugs given orally are subjected to numerous gastrointestinal secretions and to be absorbed must survive encounters with low pH and potentially degrading enzymes.

The advantage of the suspensions (dispersions) of the invention is the physiological composition of the system and the simple method of production thereof. An important advantage is that due to the oil/active ingredient suspension the preparation can be persorbed to the digestive tract through the intestinal wall. The mechanism of oral absorption provides a good distribution of the effective substance into the tissues. The dissolution rate determines the availability of the drug for absorption. Over all absorption can be controlled by manipulating the formulation, for example, reducing the particle size increases the drug's surface area, thus increasing the rate and extent of absorption. Controlled release dosage forms are designed to reduce dosage frequency, and to reduce fluctuation in plasma drug concentrations, providing a more uniform therapeutic effect. Oral controlled release forms are often designed to maintain therapeutic drug concentrations for about 12 hours. The absorption rate in accordance with the invention is controlled by embedding the drug in a matrix from which it is released slowly during transit through the gastrointestinal tract. Further the oil particles are stored in the fat tissue and thereby provide a deposition effect for the effective substance. Due to the enzymatic fat decay, the effective substance is released over a longer period of time than heretofore possible with the conventional orally administered types of pharmacologically effective substances. Again advantageously, the achieved deposition effect from the oil suspension of the invention restricts the ingestion of the active agent to at most once daily, or contrary to conventional forms which are administered several times a day. This assures improved therapeutic reliability.

Drugs for transdermal delivery must have suitable skin penetration characteristics and high potency, because the penetration rate and area of application are limited.

The bioavailability or extent to which the active agent enters the systemic circulation is determined by its physical and chemical properties, but the properties of the dosage form can also largely determine drug bioavailability.

Absorption from the oral mucosa has special significance for certain drugs, despite the fact that the surface area is small. Venous drainage from the mouth is to the superior vena cava. Significantly the drug is protected from rapid first pass metabolism by the liver. The rate of absorption through the mucous membrane is rapid. Another advantage of absorption from the oral mucosal membrane is the elimination of the effect of digestive enzymes, food intake on the rate and on the resulting concentration of the pharmacological agent during the absorption process. The exposure of the active agent to the low pHs of the stomach is also avoided.

The formulations for most types of dosage forms of the substances used in accordance with the invention can contain several types of inert adjuvant ingredients which aid in their preparation and therapeutic performance. In order to increase the patient acceptability of the product, colorants and flavorants may be added.

An important advantage of the invention arises from the fact that the formulations of the present invention contain an oil phase and are thus less apt to be colonized by bacteria, yeasts, molds or fungi. A non-toxic, non-sensitizing preservative compatible with the formulation composition can however be added. The addition of a preservative selected from the phenol or the para-hydroxybenzoate compounds can be provided for. The gel formulation may be prepared to contain 0.1 to 0.2% by weight chlorocresol, a phenol derivative or preferably 0.01 to 0.2% by weight para-hydroxybenzoate as methyl, ethyl, butyl or propyl-paraben.

Formulations of the present invention are administered orally for example for absorption through the oral mucosa or topical route by dispensing the suspension from a one milliliter calibrated dropper or if desired a two ml calibrated dropper. The oral dose can be 0.5 to 2.0 ml of the suspension; the topical dose from 0.1 to 0.5 ml. The thixotropic nature of the gel facilitates the application of small volumes of medication. High viscosity preparations may not always be desirable and convenient for the delivery of therapeutic materials. The characteristic thixotropy of the silicon dioxide stabilized oil system is such that the shearing forces of shaking, pipetting and pouring make the product behave as a mixture of much lower apparent viscosity thus facilitating oral ingestion as well as enabling the administration of the oral and topical preparations. As noted earlier, the suspensions can be formulated as creams, ointments or unguents. This can be accomplished by incorporating the suspension of active agent into a suitable base or by suitably thickening the suspension by a second addition of silica dioxide compound.

The formulation of the final dosage form of the gel for administration must respect the following criteria: (i) all components of the preparation including suspension agent, gelling agent, thickening agents, preservatives, coloring and flavoring agents should be non-toxic and compatible with the therapeutic agents; (ii) the final product should promote optimal release of the active agent to its site of action; (iii) be of adequate consistency to enhance contact time with the drug and (iv) have good patient acceptability.

Thus, in accordance with the invention suspensions, emulsions or solutions of therapeutic active agents which are water insoluble or water intolerant such as nutritional supplements, herbal products, drugs, bacteria or yeast, vitamins and minerals are prepared in edible vegetable oils including without limitation orange, lemon, soybean, cotton seed, peanut, canola, corn oil sunflower, safflower, coconut, canola, palm kernel, palm but preferably soybean oil and in some instances in mineral oils of low molecular weights. The active therapeutic agent may be in crystalline or amorphous form, it may be a liquid, as for example, an oil such as vitamin E or beta carotene or a preparation of a comminuted plant structure such as flower parts, leaf, stem, root or tree bark, or an extract of a dried plant structure, or a freeze dried preparation of a vital bacteria or yeast. The oil solvent containing the active agent as a suspension, emulsion or solution and depending on the physical and chemical characteristics and stability of the solvent/solute, may contain adjuvant ingredients as necessary for proper preparation and therapeutic performance. Colorants and flavorants may be added to increase the acceptability of the product. If the addition of a preservative is desirable a preservative selected from the phenol or the para hydroxybenzoate compounds can be added. Natural gums such as Acacin or Tragacanth can be added primarily to aid in suspension of insoluble pharmacologically active substances in the oil. Other useful synthetic mucilagenous substances including poly vinyl alcohol, methyl cellulose and carboxymethylcellulose may also be used. To the suspension of the active agent in the vegetable oil there is added the prescribed amount of silica dioxide, in proportioned amounts at the same time actively mixing with a propeller stirrer (a high shear mixer at 2000–4000 rpm). Higher mixer speeds can be utilized if the therapeutic moiety will not be denatured by the mixing action. Viscosity measurements have shown that peak viscosities which remain stable are found after short periods of vigorous mixing of silicon dioxide in the vegetable oil. Mixing to obtain a complete and uniform dispersion of the solute in the oil occurs quickly, again somewhat dependent on the physical and chemical characteristics of the therapeutic agent being dispersed. Two to 5 minutes have been found to be adequate for some systems while longer times of up to 60 minutes are required for other systems. These procedures are carried out at room temperature. The dispensing of the suspension should take advantage of the thixotropy property of the silicon dioxide. The physical and chemical characteristics of the active agent, particle size, absorption rate, required amount of active agent per dose, and end use will determine the route of administration, i.e., oral, topical or both. Generally a less viscous preparation could be used for sublingual and buccal oral application, and a more viscous preparation for oral ingestion. For topical administration the preparations of the invention may be formulated as the suspension, or the suspension distributed in a cream or cream ointment.

The invention is additionally illustrated in connection with the following examples, which are to be considered illustrative of the present invention.

EXAMPLE 1

Seven and one half grams of silicon dioxide (having a surface area of (m 2/g) of 200±25)) is added to soy bean oil in a vessel to achieve a final volume of 250 ml while mixing at a low speed of 1000–2000 rpm with a propeller stirrer high shear mixer, until all the silicon dioxide is completely dispersed and suspended in the soy bean oil. 100 grams of creatine monohydrate are then introduced under stirring into the suspension previously obtained and the stirring continued for 10 additional minutes at 7000 rpm. An ultra-fine suspension of creatine in the thickened soybean oil is obtained. The concentration of creatine monohydrate in the suspension is 40 grams per 100 ml; an oral dose of 50 ml, the recommended dose, would contain 20 grams of creatine monohydrate.

EXAMPLE 2

A suspension of creatine monohydrate and taurine was prepared by introducing the silicon dioxide, 3 grams into 85 ml of canola oil under stirring for 3–5 minutes in a commercial agitator at 1000–2000 rpm. This is followed by the introduction of 10 grams creatine monohydrate and 3 grams of taurine and the latter mixture dispersed in the thickened canola oil for 3 minutes in the agitator operating at 7000 rpm. An ultra-fine suspension of the creatinine monohydrate and taurine in the thickened canola oil with a concentration of 10 grams creatine monohydrate per 100 ml and 3 grams of taurine per 100 ml of canola oil silicon dioxide gel. The recommended oral dose is 50 ml and would contain 5 grams of creatine and 1.5 grams of taurine respectively.

EXAMPLE 3

Seven and one-half grams of silicon dioxide are added to safflower oil in a vessel to achieve a final volume of 250 ml while mixing at a low speed of 500–1000 rpm with a high shear mixer until all the silicon dioxide is completely dispersed and suspended in the safflower oil. One hundred grams of creatine monohydrate, 5 grams of L-glutamine and 12.5 grams of ribose are dry blended and then introduced under continual stirring into the suspension previously obtained. The stirring is continued for 35 minutes at 3000 rpm until an ultra-fine suspension of creatine, ribose and glutamine are obtained. The concentration of creatine monohydrate in the suspension is 40 grams per 100 ml, 2 grams per 100 ml for the glutamine, and 5 grams per 100 ml for the ribose. A 50 ml dose would contain 20 grams of creatine, 1 gram of glutamine and 2.5 grams of ribose.

EXAMPLE 4

Standardized dried ginkgo extract, 15 grams are added to a blender mixer vessel containing soybean oil to give a final volume of 100 ml, and the contents mixed at high speed. Four grams of silicon dioxide are added and the mixing continued. The concentration of Ginkgo in the suspension is 0.15 grams dried Ginkgo extract equivalent to 3.6 grams Ginkgo flavone glycosides per 100 ml of soybean oil/silicon dioxide gel the resulting preparation is suitable for peroral administration the suspension is characterized by its stability over long periods of time. The recommended dose is 150 mg twice daily and would be administered sublingually with a calibrated dropper in a 1 ml volume.

EXAMPLE 5

Seven and one half grams of silicon dioxide are added to soybean' oil in a vessel to achieve a final volume of 250 ml while mixing at a low Speed of 500–1000 rpm with a high-shear mixer until all of the silicon dioxide is completely dispersed and suspended in the soybean oil. One gram of Vitamin E (1110 IU/gram) is added to the mix. Mixing is continued at 50–1000 rpm for an additional 2–3 minutes. One hundred grams of Creatine monohydrate, 5 grams of L-glutamine and 12.5 grams of ribose are dry blended together and then introduced under continual stirring into the suspension previously obtained. The stirring is continued for 35 minutes at 3000 rpm until an ultra-fine suspension of creatine monohydrate, ribose, glutamine and Vitamin E are obtained in the soybean oil.

The concentration of Creatine monohydrate in the suspension is 40 grams per 100 ml., 2 grams per 100 ml for the glutamine, 5 grams per 100 ml for the ribose and 440 IU per 100 ml for the Vitamin E. A 50 ml dose would contain 20 grams of creatine, 1 gram of 1 gram of glutamine, 2.5 grams of ribose and 220 IU's of Vitamin E.

EXAMPLE 6

A stock suspension of 4 vitamins was prepared in mineral oil which had been gelled by addition of silicon dioxide and stirring at 2000 rpm so that 5 ml contain the following: Vitamin A (Retinol) 200,000 IU, Vitamin C (Ascorbic Acid) 20,000 mg, Vitamin D (cholecalciferol) 8,000 IU, and Vitamin E (alpha-tocopherol) 8,000 IU. This vitamin preparation was dispersed in 95 ml of a conventional and readily available polyacrylic gel with a paddle type stirrer. After thorough mixing the resultant dispersion was dispensed into appropriate containers. The resultant gel formulation is applied to the skin in approximately 1 gram amounts daily.

What is claimed is:

1. A composition suitable for oral or topical delivery of a drug or nutritional supplement to a human consisting of a drug or nutritional supplement which is water insoluble or water intolerant and selected from the group consisting of creatine, creatine monohydrate and ginkgo biloba dispersed in a carrier consisting of a stable suspension of silicon dioxide in an oil selected from the group consisting of soy bean, safflower and canola wherein said carrier is in the form of a liquid pourable gel.

2. The composition according to claim 1 wherein said drug or nutritional supplement is creatine.

3. The composition according to claim 1 wherein said drug or nutritional supplement is Ginkgo Biloba.

4. The composition according to claim 1 wherein said drug or nutritional supplement is creatine monohydrate.

5. A composition suitable for oral or topical delivery of a drug or nutritional supplement to a human consisting of creatine monohydrate and a member selected from the group consisting of amino acids, sugars, starch, glycogen and mixtures thereof dispersed in a carrier consisting of a stable suspension of silicon dioxide in an oil selected from the group consisting of soybean, safflower, and canola oil.

6. A composition suitable for oral or topical delivery of a drug or nutritional supplement to a human consisting of creatine monohydrate and taurine dispersed in a carrier consisting of a stable suspension of silicon dioxide in canola oil.

7. A composition suitable for oral or topical delivery of a drug or nutritional supplement to a human consisting of creatine monohydrate, L-glutamine and ribose dispersed in a carrier consisting of a stable suspension of silicon dioxide in safflower oil.

8. A composition suitable for oral or topical delivery of a drug or nutritional supplement to a human consisting of creatine monohydrate, L-glutamine and ribose dispersed in a carrier consisting of a stable suspension of silicon dioxide in soybean oil.

9. A composition suitable for oral or topical delivery of a drug or nutritional supplement to a human consisting of a drug which is water soluble or water intolerant selected from the group consisting of creatine, creatine monohydrate and ginkgo biloba dispersed in a carrier consisting of stable suspension of silicon dioxide in an oil selected from the group consisting of soybean oil, safflower and canola oil wherein said carrier is in the form of a member selected from the group consisting of creams, unguents, salves, gels and ointments and is adapted for topical administration.

* * * * *

UNITED STATES PATENT AND TRADEMARK OFFICE
CERTIFICATE OF CORRECTION

PATENT NO.    : 6,617,356 B2                                                Page 1 of 1
DATED         : September 9, 2003
INVENTOR(S)   : Louis P. Goodman and Dennis Bizub It is certified that error appears in the above-identified patent and that said Letters Patent is hereby corrected as shown below:

<u>Title page,</u>
Item [73], should read:
-- Assignee:    Naturally Scientific, Inc.
                10 Henderson Drive
                West Caldwell, New Jersey 07006 --

Signed and Sealed this

Twenty-seventh Day of April, 2004

JON W. DUDAS
*Acting Director of the United States Patent and Trademark Office*